United States Patent [19]

Kazmierczak et al.

[11] Patent Number: 4,983,738

[45] Date of Patent: Jan. 8, 1991

[54] REACTIVE HINDERED AMINE LIGHT STABILIZERS

[75] Inventors: Robert T. Kazmierczak; Ronald E. Mac Leay, both of Williamsville, N.Y.

[73] Assignee: Atochem North America, Inc., Philadelphia, Pa.

[21] Appl. No.: 310,408

[22] Filed: Feb. 13, 1989

Related U.S. Application Data

[63] Continuation-in-part of Ser. No. 84,602, Aug. 12, 1987, abandoned.

[51] Int. Cl.$^5$ .................. C07D 211/58; C07D 401/12
[52] U.S. Cl. ..................... 546/208; 546/187; 546/189; 546/190; 546/191; 546/207; 546/224; 546/244; 546/245; 524/99; 524/102
[58] Field of Search ............... 546/224, 187, 189, 190, 546/191, 208, 244, 245, 207

[56] References Cited

U.S. PATENT DOCUMENTS

| 3,022,345 | 2/1962 | Szmuszkovicz | 564/151 |
|---|---|---|---|
| 3,706,797 | 12/1972 | McKillip et al. | 564/151 |
| 4,095,028 | 6/1978 | Hall et al. | 560/44 |
| 4,153,596 | 5/1979 | Oertel et al. | 546/190 |
| 4,191,683 | 3/1980 | Brunetti et al. | 546/186 |
| 4,223,147 | 9/1980 | Oertel et al. | 546/190 |
| 4,309,546 | 1/1982 | Karrer | 546/208 |
| 4,336,183 | 6/1982 | Nakahara et al. | 546/19 |
| 4,348,524 | 9/1982 | Karrer et al. | 546/190 |
| 4,692,486 | 9/1987 | Gugumus | 546/188 |

FOREIGN PATENT DOCUMENTS

| 226700 | 5/1986 | Czechoslovakia | 564/208 |
|---|---|---|---|
| 22997 | 1/1981 | European Pat. Off. | 546/19 |
| 54-95649 | 7/1979 | Japan | 546/188 |
| 54-103461 | 8/1979 | Japan | 546/19 |
| 2197318 | 5/1988 | United Kingdom | 546/190 |

OTHER PUBLICATIONS

"Anionic Polymerization to Cationic Polymerization," Encyclopedia of Polymer Science and Engineering, vol. 2, pp. 83, 84 (John Wiley & Sons).
Wilson B. Lutz et al., "New Derivatives of 2,2,6,6-Tetramethylpiperidine," pp. 1695–1703 (May 1962).

Primary Examiner—Robert T. Bond
Attorney, Agent, or Firm—Panitch Schwarze Jacobs & Nadel

[57] ABSTRACT

N-(2,2,6,6-tetraalkyl-4-piperidinyl)amide-hydrazides of dicarboxylic acids contain a light stabilizing group, a heat stabilizing group, and a reactive hydrazide functionality in the same molecule. The reactive stabilizers are prepared by reacting 4-amino-2,2,6,6-tetraalkylpiperidines with diesters (or mono ester acid chlorides) of dicarboxylic acids or dialkyl itaconates followed by hydrazinolysis of the ester group of the intermediate mono esteramide. The compounds are useful for introducing permanent heat and light stability to coreactive polymers or copolymers. They are also useful in the stabilization of inert polymeric systems against the degradative effects of heat and light when merely mixed with, rather than reacted with, the polymers for which stabilization is sought.

9 Claims, No Drawings

REACTIVE HINDERED AMINE LIGHT STABILIZERS

CROSS-REFERENCE TO RELATED APPLICATION

This application is a continuation-in-part of copending U.S. patent application Ser. No. 84,602, filed Aug. 12, 1987, now abandoned.

BACKGROUND OF THE INVENTION

This invention relates to N-(2,2,6,6-tetraalkyl-4-piperidinyl) amide-hydrazides of dicarboxylic acids which contain a hindered amine light stabilizing group (photooxidative stabilizer) and a reactive hydrazide group (heat stabilizer). In addition, this invention relates to the stabilization of polymeric systems against the degradative effects of heat and/or light.

Polymers such as polyolefins (e.g., polyethylene, polypropylene, etc) styrenics (e.g., polystyrene, rubber modified polystyrene, ABS, MBS, etc.), polyvinyl chloride, polycarbonates, polyesters, polypenylene ethers, and polyamides, for example, are subject to degradation and discoloration upon exposure to heat and/or light with consequent deterioration of their mechanical properties.

Various stabilizers have been proposed to inhibit such deterioration. Hindered piperidine compounds have found extensive use in the photostabilization of polyolefins. Hydrazides have been used to prevent deterioration of polyolefins by heat, oxidation, or heavy metal contamination. Derivatives of hydrazides are also commercially available for use as polymer stabilizers. (See Encyclopedia of Polymer Science and Engineering, 2nd Ed. Vol. 2, pp. 83–84).

Four examples were found in the literature where the hindered amine moiety and the hydrazide moiety (—R—C(=O)—NH—NH$_2$, where R is not O, N, or S) are present in the same molecule.

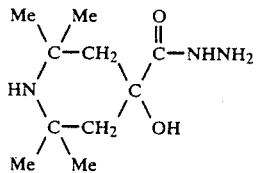

Chemical Abstracts Registry Number 66651-22-7
U.S. Pat. Nos. 4,153,596 and 4,223,147

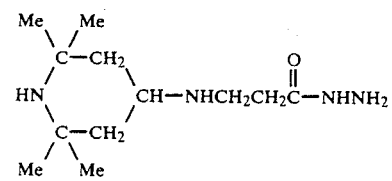

Chemical Abstracts Registry Number 66651-23-8
U.S. Pat. Nos. 4,153,596 and 4,223,147

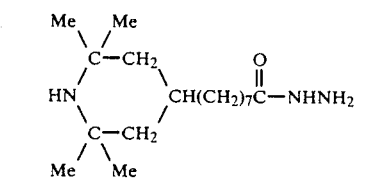

Chemical Abstracts Registry Number 72436-11-4
Japanese Patent 79/103461; CA92:59703j
Japanese Patent 79/95649; CA92:42845j

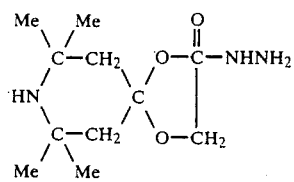

Chemical Abstracts Registry Number 77246-76-5
U.S. Pat. No. 4,336,183; CA92:217369g
European Publ. Patent Appl. 22997; CA94:176176s None of these prior art hydrazides fall under general structure I of the present invention.

SUMMARY OF THE INVENTION

This invention is directed to reactive N-(2,2,6,6-tetraalkyl-4-piperidinyl)amidehydrazides having the following formula:

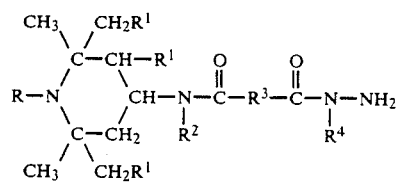

where
R is hydrogen, oxy, hydroxy, aliphatic of 1 to 20 carbons, araliphatic of 7 to 12 carbons, aliphatic acyl of 2 to 10 carbons, aryl acyl of 7 to 13 carbons, alkoxycarbonyl of 2 to 9 carbons, aryloxycarbonyl of 7 to 15 carbons, aliphatic aryl, alicyclic or araliphatic substituted carbamoyl of 2 to 13 carbons, 2-cyanoethyl, hydroxyaliphatic of 1 to 6 carbons, epoxyaliphatic of 3 to 10 carbons, or a polyalkylene oxide group of 4 to 30 carbons;

$R^1$ is hydrogen or lower alkyl of 1 to 4 carbons;

$R^2$ is hydrogen, aliphatic of 1 to 10 carbons, alicyclic of 5 to 12 carbons, araliphatic of 7 to 12 carbons, aryl of 6 to 12 carbons, 2-cyanoethyl or a radical of the formula

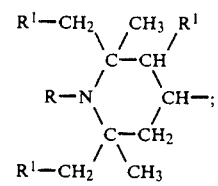

$R^3$ is a direct bond, an alkylene diradical of 1 to 14 carbons, an alkenylene diradical of 2 to 10 carbons, an oxydialkylene or thiodialkylene diradical of 4 to 10 carbons, or a substituted or unsubstituted o-, m- or p-phenylene diradical where the substituents may be lower alkyl, lower alkoxy, hydroxy, bromo, chloro, mercapto or lower alkylmercapto;

$R^2$ and $R^3$ may be linked together to form a 5-membered lactam ring; and $R^4$ is hydrogen, a primary or secondary aliphatic of 1 to 8 carbons, an araliphatic of 7 to 12 carbons or alicyclic of 5 to 12 carbons.

As used herein, the term "acyl" refers to a radical generated from a carboxylic acid by removal of the OH group to provide a free valence on the C(=O) group, for example $DC(=))$—OH would become the $DC(=O)$—substituent, referred to generally as a D acyl group.

Preferably, R, when aliphatic, is alkyl of 1 to 20 carbons, alkenyl of 3 to 8 carbons or alkynyl of 3 to 8 carbons; when araliphatic, is aralkyl of 7 to 12 carbons; the aliphatic, alicyclic and araliphatic substituents for the carbamoyl of 2 to 13 carbons preferably are alkyl, cycloalkyl and aralkyl, respectively; the hydroxy aliphatic group preferably is hydroxy alkyl of 1 to 6 carbons; and the epoxy aliphatic group preferably is epoxy alkyl of 3 to 10 carbons.

More preferably, R is hydrogen, oxy, hydroxy, alkyl of 1 to 10 carbons, alkenyl of 3 to 5 carbons, alkynyl of 3 to 5 carbons, aralkyl of 7 to 9 carbons, alkyl acyl of 2 to 8 carbons, aryl acyl of 7 to 12 carbons, alkoxycarbonyl of 2 to 7 carbons, aryloxycarbonyl of 7 to 12 carbons, hydroxyalkyl of 1 to 6 carbons, or epoxyalkyl of 1 to 6 carbons.

Preferably, $R^2$, when aliphatic, is alkyl of 1 to 10 carbons, when alicyclic, is cycloalkyl of 5 to 12 carbons, and when araliphatic, is aralkyl of 7 to 12 carbons.

Preferably, $R^3$ is a direct bond or an alkylene diradical of 1 to 7 carbons.

Preferably, $R^4$, when primary or secondary aliphatic, is a primary or secondary alkyl of 1 to 8 carbons, when alicyclic, is cycloalkyl of 5 to 12 carbons, and when araliphatic, is aralkyl of 7 to 12 carbons.

Even more preferably, R is hydrogen, acetyl, benzoyl or methyl, $R^1$ and $R^4$ are hydrogen, $R^2$ is hydrogen, methyl, butyl or a 2,2,6,6-tetramethyl-4-piperidinyl radical, and $R^3$ is a direct bond or a 1,2-ethylene diradical. Most preferably, R and $R^2$ are hydrogen and $R^3$ is a direct bond.

This invention also comprehends the stabilization of polymeric systems against the degradative effects of heat and/or light by inclusion of an effective amount of a compound of Formula I.

This invention also comprehends processes of preparing the compound of Formula I.

DETAILED DESCRIPTION OF THE PREFERRED EMBODIMENTS

The compounds of Formula I are reactive additives that can be attached to coreactive polymers to form polymer-bound additives containing photooxidative and thermal oxidative stabilizing groups. For example, the reactive N-(2,2,6,6-tetraalkyl-4-piperidinyl) amide-hydrazides can be reacted with anhydride copolymers such as styrenemaleic (SMA) copolymers, octadecene-maleic anhydride copolymers and ethylene-maleic anhydride copolymers, to name just a few. Once reacted with the coreactive polymers, the stabilizer groups become attached to the polymers and will not be lost via volatilization, migration or extraction.

The compounds of Formula I have now been discovered to be very efficient light and heat stabilizers in their own right and can be incorporated into polymeric compositions merely by mixing, rather than by reacting with coreactive polymers, to stabilize the polymers against the degradative effects of light and heat.

Non-limiting examples of reactive hindered amine light and heat stabilizers of this invention, which may also be used for light and heat stabilization of inert polymers, include the following non-limiting list of hydrazides:

(1) N-(1,2,2,6,6-pentamethyl-4-piperidinyl)-N'-aminooxamide,
(2) N-(1-benzoyl-2,2,6,6-tetramethyl-4-piperidinyl)-N'-aminooxamide,
(3) N-(1-allyl-2,2,6,6-tetramethyl-4-piperidinyl)-N'-aminooxamide,
(4) N-(1-benzyl-2,2,6,6-tetramethyl-4-piperidinyl)-N'-aminooxamide,
(5) N-(1-ethoxycarbonyl-2,2,6,6-tetramethyl-4-piperidinyl)-N'-aminooxamide,
(6) N-(1-dodecyl-2,6-diethyl-2,3,6-trimethyl-4-piperidinyl)-N'-aminooxamide,
(7) N-(2,2,6,6-tetramethyl-4-piperidinyl)-N-butyl-N'-aminooxamide,
(8) B-(2,2,6,6-tetramethyl-4-piperidinyl)-N-phenyl-N'-aminosuccinamide,
(9) N-(2,2,6,6-tetramethyl-4-piperidinyl)-N-methyl-N'-methyl-N'-aminomalonamide,
(10) N-(2,2,6,6-tetramethyl-4-piperidinyl)-N'-aminoterephthalamide,
(11) N-(2,2,6,6-tetramethyl-4-piperidinyl)-N'-butyl-N'-aminosebacamide,
(12) N-(2,2,6,6-tetramethyl-4-piperidinyl)-N'-aminododecanamide,
(13) N-(2,2,6,6-tetramethyl-4-piperidinyl)-N'-aminosuberamide,
(14) N-(2,2,6,6-tetramethyl-4-piperidinyl)-N'-aminoglutaramide,
(15) N-(2,2,6,6-tetramethyl-4-piperidinyl)-N'-amino-2-methylsuccinamide,
(16) N-(2,2,6,6-tetramethyl-4-piperidinyl)-N'-amino-2,3-dimethylsuccinamide,
(17) N-(2,2,6,6-tetramethyl-4-piperidinyl)-N'-aminopimelamide,
(18) N-(2,2,6,6-tetramethyl-4-piperidinyl)-N'-aminoundecandiamide,
(19) N-(1-beta-hydroxyethyl-2,2,6,6-tetramethyl-(4-piperidinyl)-N'-aminoadipamide,
(20) N-(1-beta-cyanoethyl-2,2,6,6-tetramethyl-4-piperidinyl)-N'-aminosuccinamide,
(21) N-(1-phenoxycarbonyl-2,2,6,6-tetramethyl-4-piperidinyl)-N'-aminooxamide,
(22) N-(2,6-diethyl-2,3,6-trimethyl-4-piperidinyl)-N'-aminooxamide, and
(23) N,N-bis-(2,2,6,6-tetramethyl-4-piperidinyl)-N'-aminooxamide.

PREPARATION OF COMPOUNDS OF THE PRESENT INVENTION

The compounds of the present invention, designated generally by Formula I may be prepared by various methods, including one or more of Methods A, B, C, D, E and F as follows. As indicated by variations within the formulas and methods, different methods may be preferred for use with different variations of Formula I.

Preparation Method A

The N-(2,2,6,6-tetraalkyl-4-piperidinyl) amide-hydrazides of Formula I where $R^4$ is hydrogen and $R^2$ and $R^3$ are not linked together, designated as Formula V, are prepared by reacting the 4-amino-2,2,6,6-tetra-alkyl-piperidines of Formula II with half ester-half acid chlorides of Formula III to form the intermediate half ester-half amides of Formula IV. The intermediate half ester-half amides are then reacted with hydrazine or hydrazine hydrate to form the compounds of Formula V.

The reaction sequence of Method A is illustrated by the following equations.

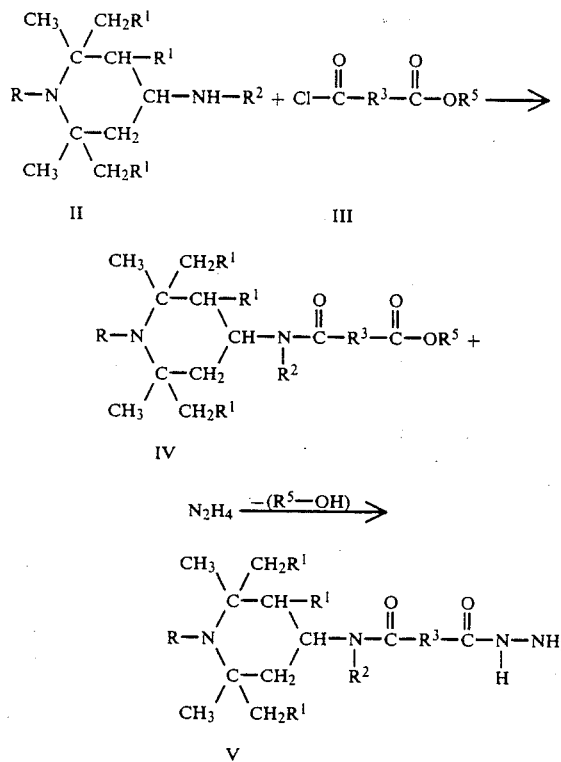

In the equations for Method A, R, $R^1$, $R^2$ and $R^3$ are as previously defined, except $R^2$ and $R^3$ are not linked together to form a lactam ring, and $R^5$ is lower alkyl of 1 to 6 carbons or phenyl and preferably, $R^5$ is methyl or ethyl.

Since HCl is liberated in the first step, it is preferable to run the reaction in the presence of a hydrogen chloride acceptor such as a tertiary amine, an inorganic base or an excess of the amine II. Preferably, a 100% excess of the amine II is used as the hydrogen chloride acceptor. The amine hydrochloride formed can be separated from the reaction mixture by filtration or may be removed by washing the reaction mixture with water. (The amine can be regenerated by neutralization with a stronger base.) The reaction can be run in a variety of non-reactive solvents, such as hydrocarbons, chlorinated hydrocarbons or ethers. Non-limiting examples of hydrocarbon solvents are xylene and toluene. Non-limiting examples of chlorinated hydrocarbons are methylene chloride, 1,2-dichloroethane and chloroform. An example of an ether is diethyl ether. Other suitable solvents would be well known to those skilled in the art.

Preferably, the reaction is run in the lower boiling solvents, such as methylene chloride, 1,2-dichloroethane or chloroform, for example, so the product can be isolated by stripping off the solvent. The reaction is exothermic, so gentle cooling is advisable to control the temperature. The intermediate IV is isolated, dissolved in a polar solvent and converted to the hydrazide by stirring with an equivalent amount or slight excess of hydrazine or hydrazine hydrate. Depending upon $R^3$, the reaction may proceed at room temperature or may require refluxing. Preferably, the hydrazinolysis reaction is carried out in methanol or ethanol at about 10° C. to about 30° C., but other solvents, such as isopropanol or ethylene glycol are also acceptable. In most cases, the compounds of Formula I can be purified by recrystallization from the lower alcohols.

Non-limiting examples of suitable mono ester acid chlorides include: the mono esters (preferably the mono methyl or ethyl esters) of phthaloyl, isophthaloyl, terephthaloyl, adipoyl, azelayoyl, succinyl, oxalyl, malonyl, fumaroyl, sebacoyl and suberoyl chlorides.

Non-limiting examples of suitable amino-substituted hindered amine light stabilizers (II) include:
4-amino-2,2,6,6-tetramethylpiperidine,
4-amino-1,2,2,6,6-pentamethylpiperidine,
4-amino-2,6-diethyl-2,3,6-trimethylpiperidine,
4-amino-2,6-diethyl-1,2,3,6-tetramethylpiperidine,
4-amino-1-(2-cyanoethyl)-2,2,6,6-tetramethylpiperidine,
4-[N-(n-butyl)amino]-2,2,6,6-tetramethylpiperidine,
4-[N-(ethyl)amino]-1-ethoxycarbonyl-2,2,6,6-tetramethylpiperidine,
4-[N-(hexyl)amino]-1-benzyl-2,2,6,6-tetramethylpiperidine,
4-amino-1-allyl-2,2,6,6-tetramethylpiperidine,
4-amino-1-benzoyl-2,2,6,6-tetramethylpiperidine,
4-[N-(methyl)amino]-1-dodecyl-2,2,6,6-tetramethylpiperidine,
4-[N-(phenyl)amino]-1,2,2,6,6-pentamethylpiperidine,
4-[N-(benzyl)amino]-2,2,6,6-tetramethyl-piperidine,
4-[N-(cyclohexyl)amino]-2,2,6,6-tetramethylpiperidine,
4-amino-2,6-diethyl-2,3,6-trimethylpiperidine, and
bis-(2,2,6,6-tetramethyl-4-piperidinyl)amine.

Non-limiting examples of suitable hydrazines include hydrazine, hydrazine hydrate and 35–85% hydrazine hydrate.

Preferably, the amine II is 4-amino-2,2,6,6-tetramethylpiperidine or bis-(2,2,6,6-tetramethyl-4-piperidinyl)amine, the acid chloride is ethyl (or methyl) oxalyl chloride or ethyl (or methyl) succinyl chloride and the hydrazine is 85% hydrazine hydrate.

Most of the amines of Formula II can be prepared by reductive amination of triacetonamine (or its alkylated analogs) or by alkylation or acylation of triacetonamine followed by reductive amination (See U.S. Pat. No. 4,191,683 or W. B. Lutz, S. Lazarus and R. I. Meltzer, J. Org. Chem. 27, 1695–1703 (1962)). The aliphatic (e.g. alkylated) and acylated derivatives (i.e., where R is alkyl, alkenyl, aralkyl, aliphatic acyl, aryl acyl, alkoxycarbonyl, aryloxycarbonyl, alkyl, aryl, cycloalkyl or aralkyl substituted carbamoyl, 2-cyanoethyl, or hydroxyalkyl, for example) can be prepared by alkylating or acylating the unsubtituted (i.e., where R is hydrogen) intermediate half ester-half amide IV by techniques well known in the art (e.g., acylation with acid chlorides, chloroformates, carbamoyl chlorides, isocyanates, etc., or alkylation with alkyl halides or epoxides) (see U.S. Pat. Nos. 4,348,524 and 4,191,683), followed by hydrazinolysis in a polar solvent.

The mono esters of the diacid chlorides are either commercially available or can be readily prepared by methods well known in the art from the corresponding mono esters of the dicarboxylic acids and chlorinating agents such as thionyl chloride, phosgene, phosphorous trichloride or phosphorous pentachloride.

Preparation Method B

The N-(2,2,6,6-tetraalkyl-4-piperidinyl) amide-hydrazides of Formula VIII may also be prepared by reacting the amino compounds of Formula II with essentially equivalent amounts or an excess of a dicarboxylic acid diester of Formula VI to form the intermediate half ester-half amide of Formula VII. The intermediate VII is then reacted with hydrazine or hydrazine hydrate to form the compounds I where $R^4$ is hydrogen and $R^6$ is the same as $R^3$, designated as Formula VIII, with the provisos that $R^6$ may not be an alkenylene or ethylene diradical and $R^2$ and $R^6$ are not linked together.

The reaction sequence of Method B is illustrated by the following equations:

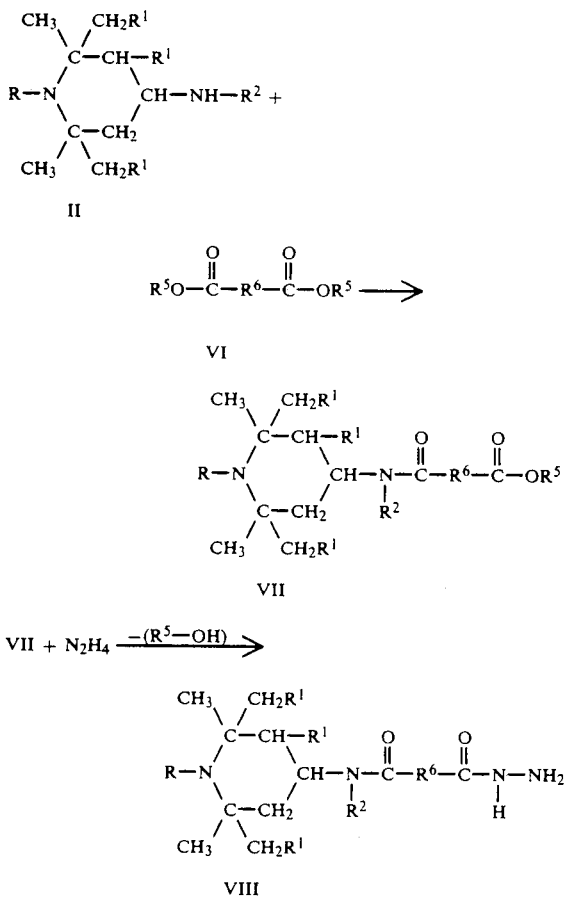

In the equations of Method B, R, $R^1$, $R^2$ and $R^5$ are as previously defined, $R^6$ is the same as $R^3$, except $R^6$ may not be an alkenylene diradical or an ethylene diradical and $R^2$ and $R^6$ are not linked together to form a lactam ring.

The reactions are preferably run neat, or in alcoholic or glycol solvents and most preferably neat or in methanol if the diesters are activated. The amines II react quite readily with the oxalic acid diesters VI at room temperature and gentle cooling is advisable in the early stages of the reaction to minimize side reactions. In the case of the other diesters (i.e., where $R^6$ is not a direct bond), heating or refluxing is necessary. The reactions can be monitored by gas chromatography and depending upon the starting amines and diesters, the reaction temperature can be adjusted up or down to speed up or slow down the reaction. In some cases it is preferable to distill off the alcohol as it forms.

When using dialkyl oxalates in methanol or ethanol, it is preferable to cool the alcohol solution of the oxalate below room temperature (5°-10° C.) before adding the amine and then allowing the temperature to rise to room temperature or above over the course of ½ to 1 hour. After the oxalate is converted to the half ester-half amide VII, an equivalent amount of hydrazine or hydrazine hydrate is added. The hydrazine readily reacts with the half-ester to form the amide-hydrazide. Any unreacted dialkyl oxalate is readily converted to insoluble oxalic acid dihydrazide which is removed by filtration. Depending upon the amount of alcohol present, the reaction mixture may have to be heated to dissolve all the product before filtering off the oxalic acid dihydrazide. The product is isolated by stripping off the solvent or by cooling the filtrate and crystallizing out the product.

When using dialkyl oxalates, the first step of the reaction sequence is preferably run in excess dialkyl oxalate to minimize side products. The excess oxalate is removed, preferably by vacuum stripping, and the hydrazinolysis of the intermediate half ester-half amide is preferably carried out in methanol, ethanol, propanol, or isopropanol.

When using diesters of other dicarboxylic acids, more severe heating conditions are required for both steps. However, the reactions can be monitored by infrared spectroscopy, or liquid or gas chromatography, and the heating conditions and length of reaction adjusted accordingly.

Suitable amines II are those illustrated for Method A. Likewise the same hydrazines are suitable for both Methods A and B. Suitable diesters include, for example and without limitation, the methyl, ethyl, propyl, isopropyl and phenyl diesters or mixtures thereof of oxalic, malonic, substituted malonic, glutaric, adipic, 2-methylglutaric, 3-methylglutaric, 2,2-dimethylglutaric, 3,3-dimethylglutaric, pimelic, adipic, suberic, azelaic, sebacic, undecanedioic, 1,10-decanedicarboxylic, 1,12-dodecanedicarboxylic, o-, m- and p- phthalic and 3,3,'-thiodipropionic acids. Diesters of fumaric acid and succinic acid were found to be unacceptable in this method.

Preferably, the amine is 4-amino-2,2,6,6-tetramethylpiperidine, the diester is diethyl oxalate, and the hydrazine is 85% hydrazine hydrate, the first step is run in excess diethyl oxalate and the hydrazinolysis step is run in methanol.

Preparation Method C

The N-(2,2,6,6-tetraalkyl-4-piperidinyl) amide-hydrazides of Formula VIII may also be prepared by reacting hydrazine or hydrazine hydrate with an excess of a dicarboxylic acid diester of Formula VI to form the intermediate half ester-half hydrazide of Formula IX (U.S. Pat. No. 3,022,345, Example 5A). The intermediate IX is then separated from the excess diester and reacted with essentially an equivalent amount or slight excess of an amino compound of Formula II. The method is limited to those compounds of Formula I wherein $R^6$ is the same as $R^3$, and is not an alkenylene or ethylene diradical, $R^4$ is hydrogen and $R^2$ and $R^6$ are not linked together, designated as Formula VIII.

The reaction sequence of Method C is illustrated by the following equations:

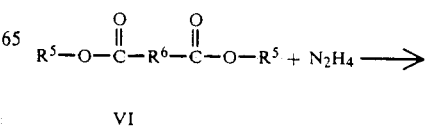

VI

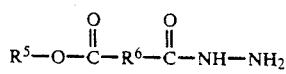

IX

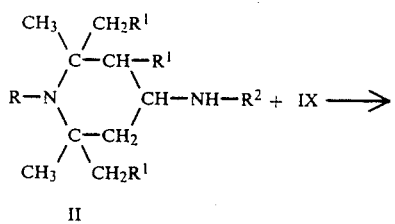

VIII

In the equations for Method C, R, $R^1$, $R^2$, $R^5$ and $R^6$ are as previously defined, $R^6$ is the same as $R^3$, except $R^6$ may not be an alkenylene diradical or an ethylene diradical, and $R^2$ and $R^6$ are not linked together to form a lactam ring.

The reactions of the hydrazine with the diester VI are preferably run neat or in alcohol or glycol solvents and most preferably in lower alcohol solvents. The reaction with oxalate diesters is preferably run at low temperatures with excess diester to selectively form the half ester-half hydrazide (IX where $R^6$ is a direct bond) instead of oxalic acid dihydrazide. With non-activated diesters, i.e., $R^6$ is not a direct bond, warming, refluxing or prolonged stirring may be necessary to form the half ester-half hydrazide. The reactions can be monitored by gas or liquid chromatography.

The half ester-half hydrazides IX are separated from any excess diester, preferably by crystallization from a solvent in which the diester is soluble. Preferably, the crystallization is performed in a lower alcohol solvent such as methanol, ethanol, propanol or isopropanol (below room temperature if necessary).

The purified half ester-half hydrazide is then reacted with a 4-amino-2,2,6,6-tetraalkylpiperidine of Formula II, preferably where $R^2$ is hydrogen. The reaction is preferably run neat or in alcohol or glycol solvents and most preferably in lower alcohol solvents. The reactions can be monitored by gas or liquid chromatography and depending upon the starting amine of Formula II and the half ester-half hydrazide of Formula IX, the reaction temperature can be adjusted up or down to speed up or slow down the reaction. If the reaction is run in a lower alcohol solvent, the reaction may be run under pressure to increase the reaction temperature.

Suitable amines II are those illustrated for Method A. Likewise, the same hydrazines are suitable for Methods A, B and C. Suitable diesters include the same diesters illustrated for Method B.

Preferably, the diester is diethyl oxalate, the hydrazine is 85% hydrazine hydrate and the amine is 4-amino-2,2,6,6-tetramethylpiperidine.

Preparation Method D

The cyclic lactam compounds generally represented by Formula XII, may be prepared by reacting 4-amino-2,2,6,6-tetraalkylpiperidines of Formula IIA corresponding to Formula II, where $R^2$ is hydrogen, with dialkyl itaconates of Formula X to form the intermediate half ester-half amide of Formula XI (which is Formula IV where $R^2$ and $R^3$ are linked together). The half ester-half amide is then converted to the hydrazide in the same manner as in Method A.

The reaction sequence of Method D is illustrated by the following equations:

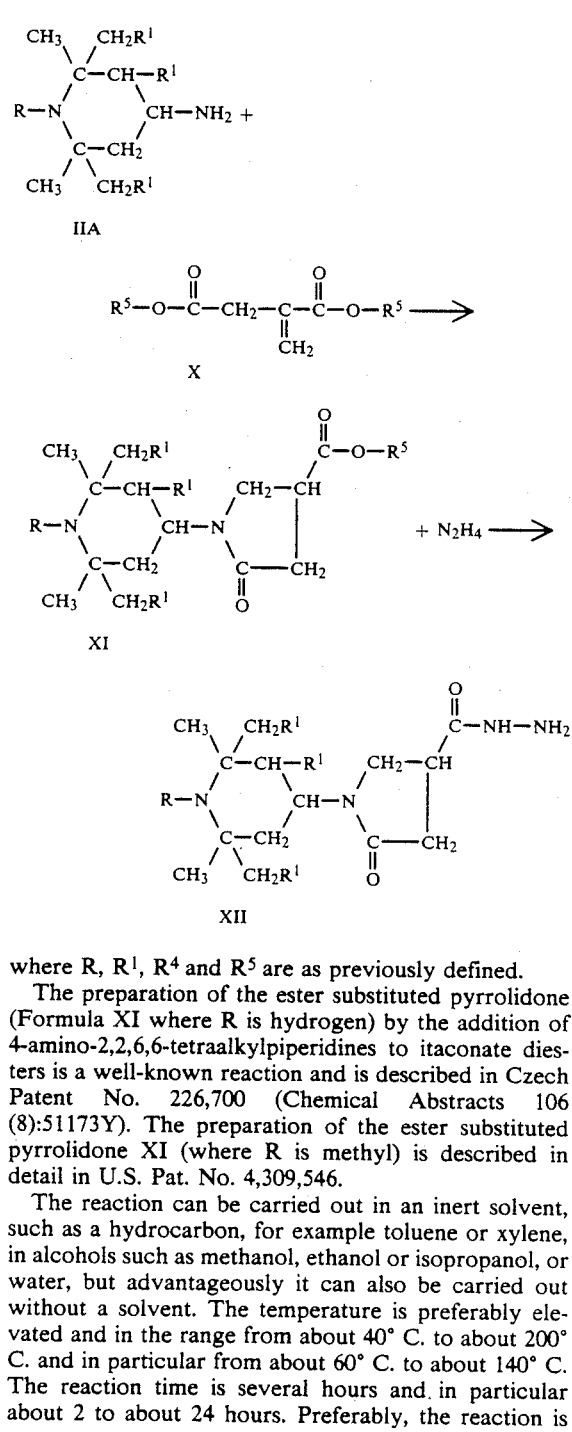

where R, $R^1$, $R^4$ and $R^5$ are as previously defined.

The preparation of the ester substituted pyrrolidone (Formula XI where R is hydrogen) by the addition of 4-amino-2,2,6,6-tetraalkylpiperidines to itaconate diesters is a well-known reaction and is described in Czech Patent No. 226,700 (Chemical Abstracts 106 (8):51173Y). The preparation of the ester substituted pyrrolidone XI (where R is methyl) is described in detail in U.S. Pat. No. 4,309,546.

The reaction can be carried out in an inert solvent, such as a hydrocarbon, for example toluene or xylene, in alcohols such as methanol, ethanol or isopropanol, or water, but advantageously it can also be carried out without a solvent. The temperature is preferably elevated and in the range from about 40° C. to about 200° C. and in particular from about 60° C. to about 140° C. The reaction time is several hours and in particular about 2 to about 24 hours. Preferably, the reaction is carried out in an inert atmosphere, for example, under nitrogen. The alcohol formed is advantageously removed from the reaction mixture and preferably is distilled off.

The intermediate XI is isolated and dissolved in a polar solvent and converted to the hydrazide by stirring with an equivalent amount or slight excess of hydrazine or hydrazine hydrate. The reaction proceeds at room temperature, but may be accelerated by heating. Preferably, the hydrazinolysis reaction is carried out in methanol or ethanol at about 10° C. to about 65° C. The products of Formula XII can be purified by recrystallization from the lower alcohols.

Non-limiting examples of suitable itaconate diesters include the dimethyl, diethyl, dipropyl, diisopropyl and dibutyl diesters.

Non-limiting examples of suitable 4-amino-2,2,6,6-tetraalkylpiperidines (Formula IIA) include 4-amino-2,2,6,6-tetramethylpiperidine, 4-amino-1,2,2,6,6-pentamethylpiperidine, 4-amino-2,6-diethyl-2,3,6-trimethylpiperidine, and 4-amino-2,6-diethyl-1,2,3,6-tetramethylpiperidine.

Preferably, the diester is dimethyl itaconate, the amine IIA is 4-amino-2,2,6,6-tetramethylpiperidine and the hydrazine is 85% hydrazine hydrate.

Preparation Method E

The N-(2,2,6,6-tetraalkyl-4-piperidinyl) amide-hydrazides of Formula I, where $R^4$ is hydrogen and $R^3$ is a direct bond, designated as Formula XV, may also be prepared by reacting the amino compounds of Formula II with essentially equivalent amounts of an oxamate of Formula XIII, where $R^5$ is lower alkyl or phenyl, preferably methyl or ethyl, to form an N-(2,2,6,6-tetraalkyl-4-piperidinyl) oxamide of Formula XIV. The N-(2,2,6,6-tetraalkyl-4-piperidinyl)oxamide is isolated and then reacted with an equivalent or excess of hydrazine or hydrazine hydrate to displace ammonia and form the compounds of Formula I where $R^4$ is hydrogen and $R^3$ is a direct bond.

The reaction sequence of Method E is illustrated by the following equations.

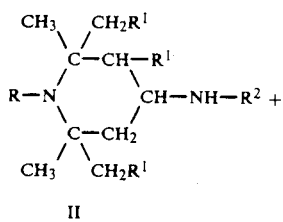

II

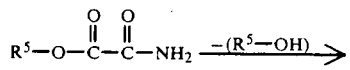

XIII

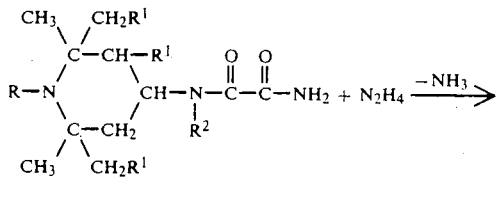

XIV

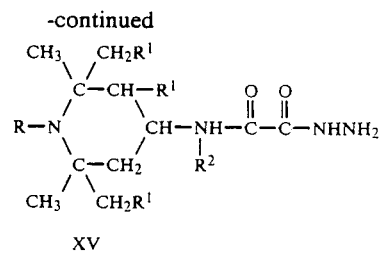

XV

In the equations for Method E, R, $R^1$, $R^2$ and $R^5$ are as previously described.

The reactions are preferably run in alcohol or glycol solvents and most preferably methanol or ethanol. The amines II, preferably where R and $R^2$ are hydrogen, react quite readily with the alkyl oxamates at room temperature. Preferably, the reaction is carried out at about 20° C. to about 40° C. to avoid side reactions. The reaction can be monitored by gas chromatography and depending upon the starting amine, the reaction temperature can be adjusted up or down to speed up or slow down the reaction. The oxamide XIV is separated from the reaction by filtration and the filtrate containing some oxamide XIV can be recharged with additional alkyl oxamate XIII and amine II and the reaction repeated.

The oxamide XIV is slurried with fresh alcohol, an excess of hydrazine or hydrazine hydrate added and the reaction heated to reflux. The conversion of the oxamide XIV to the hydrazide XV can be followed by gas chromatography. The hydrazides XV are generally soluble in hot alcohol and crystallize out of solution upon cooling. Further purification can be achieved by recrystallization from methanol, ethanol or isopropanol.

Non-limiting examples of suitable amines II include: 4-amino-2,2,6,6-tetramethylpiperidine, 4-amino-2,6-diethyl-2,3,6-trimethylpiperidine, 4-amino-1,2,2,6,6-pentamethylpiperidine and 4-amino-2,6-diethyl-1,2,3,6-tetramethylpiperidine.

Non-limiting examples of suitable oxamate esters include: methyl oxamate, ethyl oxamate, propyl oxamate, isopropyl oxamate, butyl oxamate and phenyl oxamate.

Preferably, the amine is 4-amino-2,2,6,6-tetramethylpiperidine, the oxamate ester is ethyl oxamate and the hydrazine is 85–100% hydrazine hydrate.

Preparation Method F

The compounds of Formula I where $R^4$ is a primary or secondary alkyl of 1 to 8 carbons, an aralkyl of 7 to 12 carbons or a cycloalkyl of 5 to 12 carbons, designated generally by Formula XVIII, may be prepared by reacting ketone hydrazones of Formula KVI, such as acetone hydrazones of the corresponding hydrazines, with the half ester-half amides of Formulas IV to form the corresponding alkylidene hydrazides of Formula XVII which can then be hydrolyzed to the hydrazides XVIII. The method is illustrated by the following equations:

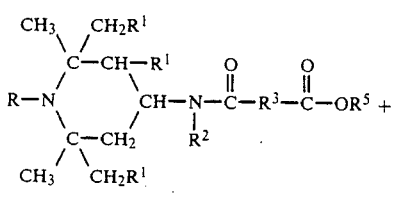

IV

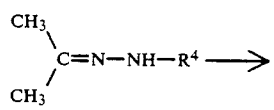

XVI

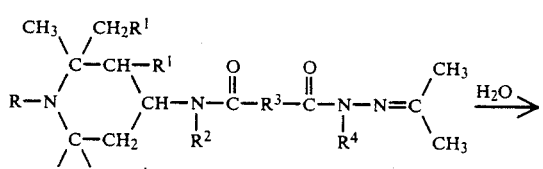

XVII

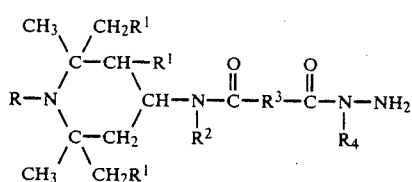

XVIII

UTILITY

The novel stabilizers of this invention are very effective additives for the stabilization of polymeric compositions which are normally subject to thermal, oxidative or actinic light degradation. At times it may be beneficial to add other additives as discussed hereinafter which will act as synergists with the hindered amine stabilizing groups of the present invention.

As used herein, the terms "polymer" or "polymeric composition(s)" include homopolymers or any type of copolymers.

The novel stabilizers of this invention can be blended with various polymeric compositions in high concentrations to form masterbatches which can then be blended with additional polymer either of the same or different type.

The amount of stabilizer used to stabilize the polymeric composition will depend on the particular polymer system to be stabilized, the degree of stabilization desired and the presence of other stabilizers in the composition. Normally, it is advisable to have about 0.01% to about 5% by weight of the 2,2,6,6-tetraalkylpiperidine moiety of the compounds of this invention present in the polymeric composition. An advantageous range is from about 0.05% to about 2% by weight of the 2,2,6,6-tetraalkylpiperidine portion of the molecule in the final composition. In most cases, about 0.1% to about 1.5% by weight is sufficient.

Non-limiting examples of polymeric compositions which may be stabilized by these novel stabilizer compounds of the present invention include:

(1) Polyolefins, such as high, low and linear low density polyethylenes, which may be optionally cross-linked, polypropylene, polyisobutylene, poly(methylbutene-1), polyacetylene and, in general, polyolefins derived from monomers having from 2 to about 10 carbon atoms, and mixtures thereof.

(2) Polyolefins derived from diolefins, such as polybutadiene and polyisoprene.

(3) Copolymers of monoolefins or diolefins, such as ethylene-propylene, propylene-butene-1, propylene-isobutylene and ethylene-butene-1 copolymer.

(4) Terpolymers of ethylene and propylene with dienes (EPDM), such as butadiene, hexadiene, dicyclopentadiene and ethylidene norbornene.

(5) Copolymers of alpha-olefins with acrylic acid or methacrylic acids or their derivatives, such as ethylene-acrylic acid, ethylene-methacrylic acid and ethylene-ethyl acrylate copolymers.

(6) Styrenic polymers, such as polystyrene (PS) and poly(p-methylstyrene).

(7) Styrenic copolymers and terpolymers such as styrene-butadiene (SBR), styrene-allyl alcohol and styrene-acrylonitrile (SAN), styrene-acrylonitrile-methacrylate terpolymer, styrene-butadiene-styrene block copolymers (SBS), rubber modified styrenics such as styrene-acrylonitrile copolymers modified with acrylic ester polymer (ASA), graft copolymers of styrene on rubbers such as polybutadiene (HIPS), polyisoprene or styrene-butadiene-styrene block copolymers (Stereon ™ products available from Firestone Synthetic Rubber and Latex Co.), graft copolymers of styrene-acrylonitrile on rubbers such as butadiene (ABS), polyisoprene or styrene-butadiene-styrene block copolymers, graft copolymers of styrene-methyl methacrylate on rubbers such as polybutadiene (MBS), butadiene-styrene radial block copolymers (e.g., KRO 3 ™ of Phillips Petroleum Co.), selectively hydrogenated butadiene-styrene block copolymers (e.g., Kraton G ™ from Shell Chemical Co.) and mixtures thereof.

(8) Polymers and copolymers derived from halogen-containing vinyl monomers, such as poly(vinyl chloride), poly(vinyl fluoride), poly(vinylidene chloride), poly(vinylidene fluoride), poly(tetrafluoroethylene) (PTFE), vinyl chloride-vinyl acetate copolymers, vinylidene chloride vinyl acetate copolymers and ethylene-tetrafluoroethylene copolymers.

(9) Halogenated rubbers, such as chlorinated and/or brominated butyl rubbers or polyolefins and fluoroelastomers.

(10) Polymers and copolymers derived from alpha, beta-unsaturated acids, anhydrides, esters, amides and nitriles or combinations thereof, such as polymers or copolymers of acrylic and methacrylic acids, alkyl and-/or glycidyl acrylates and methacrylates, acrylamide and methacrylamide, acrylonitrile, maleic anhydride, maleimide, the various anhydride containing polymers and copolymers described in this disclosure, copolymers of the polymers set forth in this paragraph and various blends and mixtures thereof, as well as rubber modified versions of the polymers and copolymers set forth in this paragraph.

(11) Polymers and copolymers derived from unsaturated alcohols or their acylated derivatives, such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene-vinyl alcohol copolymers.

(12) Polymers and copolymers derived from unsaturated amines, such as poly(allyl melamine).

(13) Polymers and copolymers derived from epoxides, such as polyethylene oxide, polypropylene oxide and copolymers thereof, as well as polymers derived from bis-glycidyl ethers.

(14) Poly(phenylene oxides), poly(phenylene ethers) and modifications thereof containing grafted polystyrene or rubbers, as well as their various blends with polystyrene, rubber modified polystyrenes or nylon.

(15) Polycarbonates and especially the aromatic polycarbonates, such as those derived from phosgene and bisphenols such as bisphenol-A, tetrabromobisphenol-A and tetramethylbisphenol-A.

(16) Polyesters derived from dicarboxylic acids and diols and/or hydroxycarboxylic acids or their corresponding lactones, such as polyalkylene phthalates (e.g., polyethylene terephthalate (PET), polybutylene terephthalate (PBT), and poly (1,4-dimethylcyclohexane terephthalate) or copolymers thereof) and polylactones, such as polycaprolactone.

(17) Polyarylates derived from bisphenols (e.g., bisphenol-A) and various aromatic acids, such as isophthalic and terephthalic acids or mixtures thereof.

(18) Aromatic copolyester carbonates having carbonate as well as ester linkages present in the backbone of the polymers, such as those derived from bisphenols, iso- and terephthaloyl chlorides and phosgene.

(19) Polyurethanes and polyureas.

(20) Polyacetals, such as polyoxymethylenes and polyoxymethylenes which contain ethylene oxide as a comonomer.

(21) Polysulfones, polyethersulfones and polyimidesulfones.

(22) Polyamides and copolyamides which are derived from diamines and dicarboxylic acids and/or from aminocarboxylic acids or the corresponding lactones, such as the following nylons: 6, 6/6, 6/10, 11 and 12.

(23) Polyimides, polyetherimides, polyamideimides and copolyetheresters.

(24) Cross-linked polymers which are derived from aldehydes on the one hand and from phenols, ureas and melamine on the other hand, such as phenol-formaldehyde, urea-formaldehyde and melamine-formaldehyde resins.

(25) Alkyl resins, such as glycerolphthalic acid resins and mixtures thereof with melamine-formaldehyde resins.

(26) Blends of vinyl monomers and unsaturated polyester resins which are derived from copolyesters of saturated and unsaturated dicarboxylic acids with polyhydric alcohols, as well as from vinyl compounds (crosslinking agents) and also halogen-containing, flame resistant modifications thereof.

(27) Natural polymers such as cellulose and natural rubber, as well as the chemically modified homologous derivatives thereof, such as cellulose acetates, cellulose propionate, cellulose butyrate and the cellulose ethers such as methyl and ethyl cellulose.

In addition, the novel stabilizers of this invention may be used to stabilize various combinations or blends of the above polymers or copolymers. They are particularly useful in the stabilization of polyolefins, acrylic coatings, styrenics, rubber modified styrenics, poly(phenylene oxides) and their various blends with styrenics, rubber-modified styrenics or nylon.

The novel hindered amine light and heat stabilizers of this invention can be used together with other additives to further enhance the properties of the finished polymer. Examples of other additives that can be used in conjunction with the stabilizers of this invention include antioxidants, such as alkylated monopohenols, alkylated hydroquinones, hydroxylated thiodiphenyl ethers, alkylidene-bisphenols, hindered phenolic benzyl compounds, acylaminophenols, esters of 2-(3,5-di-t-butyl-4-hydroxyphenyl) propionic acid, esters of 2-(5-t-butyl-4-hydroxy-3-methylphenyl)propionic acid, 2-(3,5-di-t-butyl-4-hydroxyphenyl)propionic acid amides; UV absorbers and light stabilizers such as 2-(2'-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, other hindered amine light stabilizers, other additives such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, both organic and inorganic flame retardants and non-dripping agents, melt flow improvers and antistatic agents. Numerous examples of suitable additives of the above type are given in Canadian Patent No. 1,190,038.

The following examples are presented to provide a more detailed explanation of the present invention and are intended as illustrations and not limitations of the invention.

EXAMPLE 1

Preparation of
N-(2,2,6,6-tetramethyl-4-piperidinyl)-N'-aminosuccinamide

Into a 3-neck 500 ml round bottom flask were weighed 31.5 grams (0.2 mole) of 4-amino-2,2,6,6-tetramethylpiperidine and 30.3 grams (0.3 mole) of triethylamine. The amines were diluted with 200 ml methylene chloride and the flask was equipped with a magnetic stirrer, thermometer, reflux condenser, and dropping funnel containing 32.9 grams (0.2 mole) ethyl succinyl chloride. The flask and its contents were cooled in an ice bath to 5° C. and the acid chloride was added dropwise to the stirring solution over ½ hour while holding the temperature between 5°-15° C. After the addition was complete, the ice bath was removed and the solution was stirred an additional hour. The methylene chloride solution was washed three times with 100 ml portions of water, dried over anhydrous $Na_2SO_4$, filtered and the methylene chloride stripped off on a rotating evaporator under reduced pressure. The residue was an orange-yellow viscous liquid weighing 38.2 grams. An infrared (IR) scan of the residue showed a strong NH band at 3300 cm$^{-1}$, two strong carbonyl peaks at 1730 cm$^{-1}$ and 1640 cm$^{-1}$, and an amide band at 1550 cm$^{-1}$.

The residue was dissolved in 200 ml of ethanol and transferred to a 500 ml, 3-neck flask equipped with a magnetic stirrer, thermometer and dropping funnel containing 26.4 grams of 85% hydrazine hydrate. The hydrazine hydrate was added dropwise over 5 minutes at room temperature. The reaction was stirred 1 hour at room temperature and then allowed to stand overnight. An IR scan indicated there was a small amount of unreacted ester (shoulder at 1730 cm$^{-1}$). The reaction mixture was refluxed for 1 hour. The ethanol, water, and residual hydrazine were stripped off on a rotating evaporator under vacuum leaving a mushy solid. The solids were slurried in methylene chloride, filtered off and air dried. The dry product weighed 28.2 grams, and was purified by recrystallization from isopropanol. The purified product melted at 208°–210° C. The infrared spectra of the product (nujol mull) contained a very sharp NH peak at 3300 cm$^{-1}$ and a broad NH band centered at 3230 cm$^{-1}$, a strong carbonyl band with shoulders centered at 1610 cm$^{-1}$ and an amide band at 1550 cm$^{-1}$. The ester band at 1730 cm$^{-1}$ was not present.

EXAMPLE 11

Preparation of N-(2,2,6,6-tetramethyl-4-piperidinyl)-N'-aminomalonamide

Into a 3-neck 250 ml round bottom flask were weighed 15.6 grams (0.1 mole) of 4-amino-2,2,6,6-tetramethylpiperidine and 10.1 grams (0.1 mole) of triethylamine. The amines were diluted with 100 ml of methylene chloride; the flask was equipped with a magnetic stirrer, thermometer, reflux condenser, and dropping funnel containing 11.8 grams (0.078 mole) of ethyl malonyl chloride. The ethyl malonyl chloride was added dropwise to the stirring solution of the amines without any cooling. The reaction was quite exothermic and the temperature rose from 22° C. to 42° C. where the refluxing methylene chloride controlled the temperature. The reaction was stirred for an additional hour while the temperature cooled to 35° C. The clear solution was allowed to stand overnight. The reaction mixture was then added to a stirring solution of 10.6 grams of sodium carbonate in 200 ml of water. The methylene chloride layer was separated and stripped off on a rotating evaporator. The residue weighed 17 9 grams. An infrared scan of the residue showed a strong carbonyl band at 1740 cm$^{-1}$ (ester), a carbonyl band at 1660–1680 cm$^{-1}$ (amide), and an amide band at 1550 cm$^{-1}$. An additional 1.1 grams of intermediate was obtained by back-extracting the aqueous layer with another 100 ml of methylene chloride and stripping off the solvent.

The intermediate residue was dissolved in 100 ml of ethanol in a 250 ml 3-neck flask equipped with a reflux condenser, a thermometer, a magnetic stirrer, and a dropping funnel containing 85% hydrazine hydrate (11.8 g, 1.2 mole). The hydrazine hydrate was added over 5 minutes and then the reaction was stirred an additional 1¼ hours at room temperature, warmed to reflux, and refluxed 2 hours. (Gas chromatography indicated the hydrazinolysis was completed after the 1 hour stir at room temperature). The reaction was cooled to 60° C. and filtered through a fluted filter to remove a small amount of insoluble material. The filtrate was then stripped to dryness on a rotating evaporator under vacuum. The pink residue weighed 18.8 grams. The color may have carried over from the starting ethyl malonyl chloride. The crude product was recrystallized from isopropanol. The infrared spectra of the product (in methylene chloride) showed a broad NH band at 3300 cm$^{-1}$, a strong carbonyl band with shoulders centered at 1680 cm$^{-1}$, and an amide band at 1550 cm$^{-1}$. The ester band at 1740 cm$^{-1}$ had completely disappeared. The recrystallized product had a melting point of 177°–179° C.

EXAMPLE III

Preparation of N-(2,2,6,6-tetramethyl-4-piperidinyl)-N'-aminooxamide

Method A

Into a 3-neck 500 ml round bottom flask was weighed 32.0 g (0.2 mole) of 4-amino-2,2,6,6-tetramethylpiperidine. The amine was diluted with 200 ml of methylene chloride and the flask was equipped as in Example I. The dropping funnel contained a solution of 13.7 grams (0.1 mole) of ethyl oxalyl chloride in 15 ml of methylene chloride. The acid chloride solution was added to the stirring amine solution over ½ hour while holding the temperature between 10°–20° C. The reaction was stirred an additional 2 hours at room temperature. The reaction mixture was washed twice with 50 ml of water and twice with 50 ml of saturated sodium bicarbonate solution, dried over anhydrous Na$_2$SO$_4$, and filtered; the methylene chloride was stripped off on a rotating evaporator under reduced pressure. The residue was a light yellow viscous liquid which slowly solidified. The residue weighed 19.8 grams (77% crude yield). An infrared spectrum of the residue showed an NH band at 3300 cm$^{-1}$, strong carbonyl bands at 1730 cm$^{-1}$ (ester) and 1680 cm$^{-1}$ (amide), and an amide band at 1530 cm$^{-1}$.

The residue was dissolved in 100 ml of ethanol in a 250 ml 3-neck flask equipped as in Example I. The dropping funnel contained 13.4 grams (0.225 mole) of 85% hydrazine hydrate which was added over 20 minutes to the stirring ethanol solution at 30° C. The reaction was stirred an additional hour. The reaction mixture was transferred to a round bottom flask and the ethanol and excess hydrazine were stripped off on a rotating evaporator leaving 21.5 grams of a light yellow viscous liquid which solidified to a white waxy solid upon standing. The crude product contained a small amount of residual solvent. The product was recrystallized from isopropanol yielding a white powder having a melting point of 153°–155° C. The infrared spectra of the product showed NH bands at 3300 cm$^{-1}$, a strong carbonyl band with shoulders centered at 1640–1670 cm$^{-1}$, a weak carbonyl band at 1600 cm$^{-1}$, and an amide band at 1530 cm$^{-1}$. The ester band at 1730 cm$^{-1}$ had completely disappeared (nujol mull). In chloroform solution the infrared spectrum had NH bands at 3300 and 3400 cm$^{-1}$, a very strong carbonyl band at 1680 cm$^{-1}$, and an amide band at 1510 cm$^{-1}$.

Method B

Into a 3-neck 500 ml round bottom flask was weighed 43.8 grams (0.3 mole) of diethyl oxalate. The diethyl oxalate was diluted with 280 ml of methanol and cooled to 5° C. in an ice water bath. The flask was equipped with a magnetic stirrer, a thermometer, a reflux condenser and an addition funnel containing 47.0 grams (0.3 mole) of 4-amino-2,2,6,6-tetramethylpiperidine. The amine was added to the stirred solution over 40 minutes at 5° C. and stirred for 1¼ hours at 20° C. Upon completion of the stirring periods the reaction mixture was cooled to 15° C. and 17.5 ml (0.3 mole) of 85% hydrazine hydrate were added dropwise over approximately 1 hour. The first 12 ml were added over 20 minutes at 15°–22° C. The remainder was added in increments over 50 minutes while following the reaction by gas chromatography. Upon disappearance of the intermediate oxamate, the reaction mixture was heated to reflux to dissolve any insoluble product. The reaction was filtered hot to remove the insoluble oxalic acid dihydrazide (side product). The filtrate was cooled to 10° C. and the white solids that formed were filtered off and vacuum dried for 2 hours at 50° C. The product weighed 48.8 grams and assayed 98.4% by gas chromatographic analysis. The infrared spectra was similar to the infrared spectra of the product obtained by Method A.

The methanol filtrate was stripped off to dryness leaving 16.3 grams of a mixture containing approximately 58% of the desired product and 34% N,N'-bis(2,2,6,6-tetramethyl-4-piperidinyl)oxamide as analyzed by gas chromatography.

Alternate Method B
Step 1

Into a 3-neck 1500 ml round bottom flask was added 730.5 grams (5.0 mole) of diethyl oxalate. The flask was equipped with a magnetic stirring bar, a thermometer, and a dropping funnel containing 156.3 grams (1.0 mole) 4-amino-2,2,6,6-tetramethylpiperidine. The amine was added dropwise to the stirring diethyl oxalate over 15 minutes while controlling the temperatures between 20° and 30° C. The reaction mixture was stirred an additional 15 minutes at room temperature. The magnetic stirrer, thermometer, and addition funnel were removed and the side necks of the flask stoppered. The flask was then placed on a rotating evaporator and the ethanol generated during the reaction was stripped off under reduced pressure at 25°-35° C. After the ethanol had been stripped off, the vacuum was released and the receiver drained of ethanol. The vacuum was reapplied and the excess diethyl oxalate stripped off by heating the flask in an oil bath at 140° C. under full vacuum. After constant weight was reached, the residue was cooled to room temperature, dissolved in 200 ml of methanol, and transferred to a 500 ml dropping funnel.

Step 2

Into a 3-neck 1 liter flask containing a magnetic stirrer, a thermometer, and the addition funnel containing the methanol solution of ethyl N-(2,2,6,6-tetramethyl-4-piperidyl)oxamate from Step 1, were added 400 ml of methanol followed by 67 grams (1.14 moles) of 85% hydrazine hydrate. The temperature of the solution was adjusted to 10° C. with a water bath. The methanol solution of the intermediate was added to the stirred hydrazine solution dropwise over 15 minutes while controlling the temperature at 10°-20 C. After the addition was completed, the reaction mixture was stirred an additional 20 minutes at room temperature and then warmed to 60°-65° C. to dissolve the product in the methanol. The warm solution was stirred 5 minutes at 60°-65° C. and then filtered warm to remove any insoluble oxalic acid dihydrazide. The filtrate was cooled with stirring to 0° C. to crystallize the product.

The crystallized product was filtered, washed with hexane, refiltered, and dried overnight in a vacuum oven at 65° C. The dry product weighed 218.5 grams and assayed 98%.

Method E

Step 1: Preparation of
N-(2,2,6,6-tetramethyl-4-piperidinyl)oxamide

Into a 3-neck, 250 ml, round bottom flask was added 30.5 g (0.25 mole) of ethyl oxamate (Aldrich Chemical Company) and 100 ml of methanol. The flask was equipped with a magnetic stirrer, thermometer, reflux condenser and addition funnel containing 39.0g (0.25 mole) 4-amino-2,2,6,6-tetramethylpiperidine. The stirrer was activated and the amine was added dropwise to the ethyl oxamate solution over 12 minutes as the temperature slowly rose to 35° C. The reaction was stirred an additional 2.5 hours and filtered. After air drying overnight, the filter cake weighed 40.4g and had a melting point of 203°-208° C.

The filtrate was transferred back to the 250 ml 3-neck flask and another 30.5g of ethyl oxamate was added. An additional 39g of 4-amino-2,2,6,6-tetramethylpiperidine were added over 7 minutes as the temperature slowly rose to 28° C. The reaction was stirred 3 hours and filtered. After air drying overnight, the filter cake weighed 50.0g and had a melting point of 198°-200° C.

The infrared spectrum (nujol mull) of the product contained a sharp NH band at 3370 cm$^{-1}$, a strong broad carbonyl band at 1670 cm$^{-1}$ and a weaker carbonyl band at 1520 cm$^{-1}$.

Step 2: Conversion of
N-(z,2,6,6-tetramethyl-4-piperidinyl) oxamide to
N-(2,2,6,6-tetramethyl-4-piperidinyl)-N'-amino-oxamide Into a 3-neck, 250 ml flask was added 50.0g (0.22 mole) N-(2,2,6,6-tetramethyl-4-piperidinyl)oxamide from Step 1 of this Method E, 150 ml methanol and 16.5g (0.33 mole) 100% hydrazine hydrate. The flask was equipped with a magnetic stirrer, thermometer and reflux condenser. The stirrer was activated and the reaction heated in an oil bath to reflux and the reaction refluxed for 6 hours. The reaction was monitored by gas chromatography. After 6 hours the conversion of the oxamide to the hydrazide was about 80% complete. The reaction mixture was filtered hot to remove a small amount (0.45g) of insolubles. The filtrate was then cooled with stirring to 25° C. and the crystals that formed were filtered off and air dried. The dry crystals weighed 31.6g. A second crop of 11.1g was obtained after allowing the filtrate to stand over a weekend.

Gas chromatographic analysis indicated the material from both crops was greater than 95% in assay. The infrared spectra were identical to the spectra of the material made by Methods A and B.

EXAMPLE IV

Preparation of
N-(2,2,6,6-tetramethyl-4-piperidinyl)-N'-aminoadipamide

Method A

Adipoyl chloride monomethyl ester was prepared from adipic acid monomethyl ester and thionyl chloride.

Into a 3-neck 500 ml round bottom flask was weighed 34.4 grams (0.22 mole) of 4-amino-2,2,6,6-tetramethylpiperidine. The amine was diluted with 200 ml methylene chloride; the flask was equipped as in Example I. The dropping funnel contained 17.9 grams (0.1 mole) of adipoyl chloride monomethyl ester. The acid chloride was added to the stirring amine solution over 10 minutes while holding the temperature below 20° C. with an ice-water bath. The reaction flask was stirred an additional 30 minutes at room temperature and then the contents in the flask were added to a solution of 10.6 grams (0.1 mole) of sodium carbonate in 200 ml of water. The mixture was stirred for 5 minutes and then was transferred to a separatory funnel. The methylene chloride layer was separated, washed with 200 ml of water, dried over anhydrous sodium sulfate, and filtered; the methylene chloride was stripped off on a rotating evaporator under reduced pressure. The residue was a light yellow viscous liquid weighing 25.5 grams. An infrared spectrum of the intermediate product showed an NH band at 3300 cm$^{-1}$ carbonyl bands at 1740 cm$^{-1}$ (ester) and 650 cm$^{-1}$ (amide), and an amide band at 1560 cm$^{-1}$.

The residue was dissolved in 200 ml of methanol and transferred to a 500 ml 3-neck flask equipped with a thermometer, magnetic stirrer, reflux condenser, and dropping funnel containing 15.2 grams (0.225 mole) of 85% hydrazine hydrate. The hydrazine hydrate was added dropwise over 10 minutes at 27°-28° C. The reaction mixture was heated to 50° C. in a water bath and stirred 1 hour at 45°-50° C. It was then allowed to stand at room temperature over the weekend. A gas chromatographic scan indicated all the intermediate adipamate had reacted. The reaction mixture was transferred to a round bottom flask and the methanol, water, and excess hydrazine were stripped off on a rotating evaporator leaving a white solid. The solid was slurried in hexane, filtered, and air dried. The product weighed 23.65 grams and had a melting point of 170°-173° C. The infrared spectra of the product (nujol mull) showed NH bands at 3240 cm$^{-1}$, strong carbonyls at 1600 cm$^{-1}$, and an amide band at 1550 cm$^{-1}$. The ester band at 1740 cm$^{-1}$ had completely disappeared. In chloroform solution the infrared spectra showed NH bands at 3240 cm$^{-1}$, 3340 cm$^{-1}$, and 3440 cm$^{-1}$, a strong carbonyl band at 1650 cm$^{-1}$, and an amide band at 1510 cm$^{-1}$.

Method B

Into a 50 ml 3-neck flask were weighed 7.4 grams (0.1 mole) of dimethyl adipate and 15.6 grams (0.1 mole) of 4-amino-2,2,6,6-tetramethylpiperidine. The flask was equipped with a magnetic stirring bar, thermometer, Dean-Stark trap, and reflux condenser. The flask was placed in an oil bath and heated to 166° C. over 1½ hours and heated an additional 4 hours with the temperature rising to 173° C.; 3.0 ml of methanol formed in the Dean-Stark trap. The reaction was cooled to room temperature and analyzed by gas chromatography and liquid chromatography. The semi-solid product was a mixture of the starting dimethyl adipate, the desired methyl N-(2,2,6,6-tetramethyl-4-piperidinyl)adipamate and N,N'-di(2,2,6,6-tetramethyl-4-piperidinyl)adipamide. The 4-amino-2,2,6,6-tetramethyl-piperidene had completely reacted.

The semi-solid mixture was slurried in 100 ml of methyl t-butyl ether and filtered to remove the diamide impurity (8.9 g). The filtrate was stripped on a rotating evaporator to remove the methyl t-butyl ether. The residue was a yellow viscous liquid (13.6 g). Gas chromatography indicated it was a mixture of approximately 70% of the desired adipamate and 25-30% dimethyl adipate.

Into a 100 ml 3-neck flask were added the crude mixture of the methyl N-(2,2,6,6-tetramethyl-4-piperidinyl)adipamate and dimethyl adipate and 50 ml of methanol. The flask was equipped with a magnetic stirrer, thermometer, reflux condenser and addition funnel containing 4.5 g (0.077 mole) of 85% hydrazine hydrate. The hydrazine hydrate was added dropwise over 5 minutes and the reaction mixture was stirred an additional 1½ hours at room temperature, heated to reflux, and refluxed 11 hours at 68° C. and filtered hot. The filtrate was cooled to room temperature and refiltered. The combined filter cake after drying weighed 2.8 grams and was primarily adipic acid dihydrazide. The filtrate was stripped on a rotating evaporator leaving 8.5 grams of a cream colored solid. The product contained approximately 1.4% residual adipic acid dihydrazide. An infrared scan of the product (chloroform solution) showed a sharp NH band at 3440 cm$^{-1}$ and a broad NH band at 3300 cm$^{-1}$, a very strong carbonyl band at 1650 cm$^{-1}$, and an amide band at 1510 cm$^{-1}$. A wet method assay indicated the product was 80% N-(2,2,6,6-tetra-methyl-4-piperidinyl)-N'-aminooxamide.

EXAMPLE V

Preparation of N-(2,2,6,6-tetramethyl-4-piperidinyl)-N'-aminoazelamide

Method A

Azelaoyl chloride monomethyl ester was prepared from azelaic acid monomethyl ester and thionyl chloride.

Methyl N-(2,2,6,6-tetramethyl-4-piperidinyl)azelamate was prepared in the same manner as the preparation of methyl N-(2,2,6,6-tetramethyl-4-piperidinyl)adipamate (Example IV) except 23.16 grams (0.1 mole) of azelaoyl chloride monomethyl ester was substituted for the adipoyl chloride monomethyl ester used in Example IV. The product was a light yellow viscous liquid weighing 32.1 grams. An infrared spectrum of the intermediate product showed an NH band at 3300 cm$^{-1}$, a strong carbonyl band at 1760 cm$^{-1}$ (ester), a strong broad carbonyl band at 1640-1660 cm$^{-1}$, and an amide band at 1550 cm$^{-1}$.

The intermediate product was dissolved in 200 ml methanol and treated with 15.2 grams (0.225 mole) of 85% hydrazine hydrate as in Example IV. After stirring for two days at room temperature, a gas chromatographic scan indicated that all of the azelamate had reacted. The reaction mixture was transferred to a 500 ml round bottom flask and the methanol, water, and excess hydrazine hydrate were stripped off. The residue was a pasty solid. It was slurried in methylene chloride and the solids were filtered off. The solids were transferred to a flask to strip off any residual methylene chloride. The flask was heated with a heat gun and the solids were melted and resolidified upon cooling. The product was a sticky solid which weighed 24.7 grams.

The infrared spectra of the product (chloroform solution) showed an NH band at 3300 cm$^{-1}$, a strong carbonyl band centered at 1640 cm$^{-1}$, and an amide band at 1520-1540 cm$^{-1}$. The ester band at 1760 cm$^{-1}$ had completely disappeared.

EXAMPLE VI

Preparation of N-(1-acetyl-2,2,6,6-tetramethyl-4-piperidinyl)-N'-aminooxamide

Methyl N-(2,2,6,6-tetramethyl-4piperidinyl)oxamate was prepared from diethyloxalate and 4-amino-2,2,6,6-tetramethylpiperidine according to the first step in Example III, Method B. The ethyl ester undergoes ester interchange in methanol to form the methyl ester.

Into a 125 ml 3-neck flask was added 18.2 grams (0.075 mole) of methyl N-(2,2,6,6-tetramethyl-4-piperidinyl)oxamate, 75 ml of methylene chloride and 8.1 grams (0.08 mole) of triethylamine. The flask was equipped with a magnetic stirrer, thermometer, reflux condenser, and addition funnel containing 5.9 grams (0.075 mole) of acetyl chloride in 10 ml of methylene chloride. The solution in the flask was cooled to 7° C. in an ice bath and the acetyl chloride solution was added dropwise while holding the temperature at 7°-9° C. The addition was exothermic and white solids formed during the addition. The reaction mixture was stirred 1 hour at 5°-15° C. Gas chromatography indicated that the starting material had disappeared and a new higher boiling material had formed. The reaction mixture was stirred into 100 ml of saturated sodium bicarbonate solution. The dark methylene chloride layer was separated and washed with an additional 50 ml of saturated sodium bicarbonate solution. The methylene chloride layer was separated, dried over anhydrous sodium sulfate, filtered, and stripped off on a rotating evaporator. The brown residue (14.5 grams) was slurried in methyl t-butyl ether and filtered. The tan filter cake was air dried and weighed 11.5 grams. The product had a melting point of 125°-129° C. An infrared scan (chloroform solution) contained strong carbonyl bands at 1675 cm$^{-1}$, 1600 cm$^{-1}$, and 1495 cm$^{-1}$, a weak carbonyl band at 1715 cm$^{-1}$, and a weak shoulder at 1745 cm$^{-1}$.

Into a 100 ml 3-neck flask was weighed 8.0 grams (0.028 mole) of methyl N-(1-acetyl-2,2,6,6-tetramethyl-4-piperidinyl)-oxamate (prepared above); 50 ml of methanol was added. The flask was equipped with a magnetic stirrer, thermometer, reflux condenser, and a dropping funnel containing 1.7 ml of (0.029 mole) of 85% hydrazine hydrate. The 85% hydrazine hydrate was added dropwise to the stirring slurry of the acetylated oxamate. The reaction temperature rose from 20° to 26° C. during the addition. The reaction was stirred for an additional hour at room temperature. A gas chromatographic scan taken 45 minutes into the stir period indicated that all of the starting oxamate had reacted to form the hydrazide. The reaction slurry was filtered and the white filter cake was air dried. A gas chromatographic scan of a methylene chloride solution of the product indicated the complete absence of the starting oxamate and the presence of a new higher boiling peak. A liquid chromatographic scan showed the presence of a single component. An infrared scan of the product in chloroform solution had strong carbonyl bands at 1660 cm$^{-1}$, 1610 cm$^{-1}$, and 1490 cm$^{-1}$. The dried product weighed 5.0 grams (m.p. 126°-129° C.).

EXAMPLE VII

Preparation of
4-Hydrazinocarbonyl-1-(2,2,6,6-tetramethyl-4-piperidinyl)-2-pyrrolidone Step 1

Preparation of 4-methoxycarbonyl-1-(2,2,6,6-tetramethyl-4-piperidinyl)-2-pyrrolidone.

Into a 2 liter 3-neck flask were added 158 grams (1.0 mole) dimethyl itaconate (97% purity from Aldrich Chemical Co.) and 350 mls of methanol. The flask was equipped with a magnetic stirrer, thermometer and dropping funnel containing 163.8 grams (1.05 mole) 4-amino-2,2,6,6-tetramethylpiperidine. The stirrer was activated and the amine was added dropwise over 5 minutes to the methanol solution. The temperature rose from 17° C. to 35° C. during the addition. The reaction mixture was then heated to reflux and refluxed for 18 hours. The reflux condenser was replaced by a distilling head and the methanol was distilled off at atmospheric pressure, leaving a white solid. The residue was dissolved in 700 ml of hot tetrahydrofuran and filtered to remove some white solids (6.2 g). The filtrate was cooled in an ice bath. The crystals that formed were filtered off and air dried. The white crystals weighed 148.3 grams and had a melting range of 119°-121° C. The product was essentially pure. Gas chromatographic and liquid chromatographic scans contained only 1 peak. The infrared spectra of the product in chloroform had strong sharp carbonyl bands at 1735 and 1675 cm$^{-1}$. A second crop weighing 126.2 grams was obtained by stripping the filtrate to dryness on a rotating evaporator.

Step 2

Conversion of 4-(methoxycarbonyl)-1-(2,2,6,6-tetramethyl-4-piperidinyl)-2-pyrrolidone to 4-(hydrazinocarbonyl)-1-(2,2,6,6-tetramethyl-4-piperidinyl)-2-pyrrolidone.

Into a 1 liter 3-neck flask were added 144.6 grams (0.512 mole) of the product from Step 1 of this Example and 250 ml of methanol. The flask was equipped with a magnetic stirrer, thermometer, reflux condenser and nitrogen purge. The stirrer was activated and after the solids dissolved in the methanol, 91.4 grams (1.54 mole) of 54% hydrazine were added. The reaction was stirred for 2½ hours at room temperature. An infrared spectra of the reaction mixture at this point indicated the ester group of the starting material at 1735 cm$^{-1}$ had been completely converted to hydrazide. The reaction was stripped on the rotating evaporator under vacuum at 50° C. to remove the methanol. The residue, a viscous liquid, was dissolved in 200 ml tetrahydrofuran, the tetrahydrofuran stripped off on a rotating evaporator under reduced pressure. The residue was dissolved in 200 ml of tetrahydrofuran and restripped, leaving a gummy solid. Approximately 200 ml of pentane were added, the mixture shaken and allowed to stand. The product slowly crystallized and after standing 5 days, the crystals were filtered off, vacuum dried and weighed. The crystals weighed 132.1 grams and had a melting point of 159°-161° C. The crystals assayed 99% as the hydrazide by acid-base titration. The infrared spectra of the product in chloroform had a strong sharp carbonyl band at 1675 cm$^{-1}$ and a weaker carbonyl band at 1630 and 1485 cm$^{-1}$.

Examples VIII-XVIII

Preparation, Weathering and Evaluation of Tensile Bars Containing HALS Hydrazides of Formula I Dry blends of Himont 6501 polypropylene, the particular HALS hydrazide of Formula I and optionally a small amount of a hindered phenol antioxidant (Irganox 1076), were prepared in a polyethylene container (for composition, see Table I). The blends were shaken well to assure a good dispersion of the additives in the polypropylene. The blends were extruded on a Brabender Prep Center Extruder Model No. 1340 having a 1¼ inch screw diameter with a length to diameter ratio of 25:1. The extruder was operated at a screw speed of 30 RPM and all the heating zones were controlled at 200° C. The first 100 grams of extrudate were used to purge out the extruder between runs and was discarded. The remaining extrudate was air-cooled and pelletized. The concentration of the 2,2,6,6-tetramethyl-4-piperidinyl group in the polypropylene was approximately 0.3%. The concentration of the Irganox 1076 (when used) was approximately 0.25%. UV-Chek AM-340 was included in some blends as a synergist at a concentration of 0.22%.

The pellets were injection molded in a Newbury 25-ton injection molding machine at 400° F. into 7⅜"=¾" tensile bars. A control sample containing only Irganox 1076 and control samples containing Irganox 1076 and Ciba-Geigy's Chimasorb 944 and Tinuvin 770 were included for comparison.

The tensile bars were placed in a QUV Accelerated Weathering Tester (Q Panel Company) for various exposure times. The QUV operated with an 8-hour light cycle using UV-B bulbs at 60° C. and a 4-hour condensation cycle at 50° C. Samples were placed in the QUV and withdrawn periodically at the same time of day. The tensile bars were pulled on an instrumented Instron (Model 4204) according to ASTM Procedure 638. The minimum QUV exposure time required to obtain a brittle break in the Instron test was determined. A result was considered a brittle break when the tensile bar snapped before 15% elongation was obtained. The QUV time interval required to generate spotting and clouding of the surface of the tensile bars was also noted.

Tensile bars were also exposed to UV-A bulbs in a QUV under the same conditions for 60 days. The tensile bars were then pulled on the Instron. A brittle break was considered a failure and greater than 15% elongation was considered passing.

The results are summarized in Table 1.

R is hydrogen, oxy, hydroxy, unsubstituted aliphatic of 1 to 20 carbons, unsubstituted araliphatic of 7 to 12 carbons, unsubstituted aliphatic acyl of 2 to 10 carbons, unsubstituted aryl acyl of 7 to 13 carbons, alkoxycarboxyl of 2 to 9 carbons, unsubstituted aryloxycarbonyl of 7 to 15 carbons, unsubstituted aliphatic, unsubstituted aryl, unsubstituted alicyclic or unsubstituted araliphatic substituted carbamoyl of 2 to 13 carbons, 2-cyanoethyl, unsubstituted hydroxyaliphatic of 1 to 6 carbons, unsubstituted epoxyaliphatic of 3 to 10 carbons or a polyalkylene oxide group of 4 to 30 carbons;

$R^1$ is hydrogen or lower alkyl of 1 to 4 carbons;

$R^2$ is hydrogen, unsubstituted aliphatic of 1 to 10 carbons, unsubstituted alicyclic of 5 to 12 carbons, unsubstituted araliphatic of 7 to 12 carbons, unsubstituted aryl of 6 to 12 carbons, 2-cyanoethyl or a radical of the formula

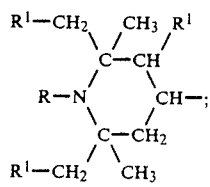

$R^3$ is a direct bond, an alkylene diradical of 1 to 14 carbons, an alkenylene diradical of 2 to 10 carbons, an oxydialkylene or thiodialkylene diradical of 4 to 10 carbons or a substituted or unsubstituted o-, m- or p-phenylene diradical where the substiuents may be lower alkyl, lower alkoxy, hydroxy, bromo, chloro, mercapto or lower alkylmercapto;

TABLE I

| | | | Stabilization of Polypropylene with HALS Hydrazides of Formula I | | | | | | |
|---|---|---|---|---|---|---|---|---|---|
| Example # | HALS COMPOUND (Example #) | GRAMS | POLY-PROPY-LENE GRAMS | IRGANOX 1076 GRAMS | UV-CHECK AM-340 GRAMS | DAYS TO SPOTTING IN QUV-B | DAYS TO BRITTLE BREAK IN QUV-B | PASS-FAIL 60 DAYS IN QUV-A | 80 DAYS in QUV-A |
| VIII | III | 2.3 | 445 | — | — | >50 <60 | >50 <60 | Pass | Pass |
| IX | III | 2.3 | 445 | 1.1 | — | >50 <60 | >50 <60 | NT | NT |
| X | III | 2.3 | 445 | — | 1.0 | >70 | >70 | Pass | Pass |
| XI | III | 2.3 | 445 | 1.1 | 1.0 | >70 | >70 | NT | Pass |
| XII | I | 2.55 | 445 | — | — | 35 | >40 <50 | Pass | Pass |
| XIII | VII | 2.7 | 445 | — | — | >35 <40 | >40 <50 | Pass | NT |
| XIV | VII | 2.7 | 445 | 1.1 | — | >35 <40 | >40 <50 | Pass | NT |
| XV | VII | 2.7 | 445 | — | 1.0 | >70 | >70 | Pass | NT |
| CONTROLS | | | | | | | | | |
| XVI | — | — | 445 | 1.1 | — | 6 | 5 | Fail | |
| XVII | A | 2.85 | 445 | 1.1 | — | 35 | >15 <25 | Fail | |
| XVIII | B | 2.30 | 445 | 1.1 | — | >35 | >20 <25 | Fail | |

A = Chimasorb 944 Ciba-Geigy's N,N'-Bis(2,2,6,6-tetramethyl-4-piperidinyl)-1,6-hexanediamine polymer with 2,4,6-trichloro-1,3,5-trimethyl-1,2-pentanamine
B = Tinuvin 770 Ciba-Geigy's Di-(2,2,6,6-tetramethyl-4-piperidinyl) sebacate
Irganox 1076 = Ciba-Geigy's octadecyl 3,5-Di-t-butyl-4-hydroxyhydrocinnamate
UV-Chek AM-340 = Ferro Corp's 2,4-Di-t-butylphenyl 3,5-Di-t-butyl-4-hydroxybenzoate
NT = Not Tested

We claim:
1. A compound of the formula

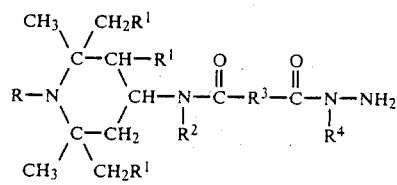

where $R^2$ and $R^3$ may be linked together to form a 5-membered lactam ring; and $R^4$ is hydrogen, a primary or secondary unsubstituted aliphatic of 1 to 8 carbons, unsubstituted araliphatic of 7 to 12 carbons or unsubstituted alicyclic of 5 to 12 carbons.

2. The compound of claim 1 where R is hydrogen, oxy, hydroxy, alkyl of 1 to 10 carbons, alkenyl of 3 to 5 carbons, alkynyl of 3 to 5 carbons, aralkyl of 7 to 9 carbons, alkyl acyl of 2 to 8 carbons, unsubstituted aryl acyl of 7 to 12 carbons, alkoxycarbonyl of 2 to 7 carbons, unsubstituted aryloxycarbonyl of 7 to 12 carbons, substituted carbamoyl of 2 to 13 carbons where the substituents for the carbamoyl of 2 to 13 carbons are alkyl, cycloalkyl or aralkyl, or hydroxyalkyl of 1 to 6 carbons, or epoxyalkyl of 3 to 6 carbons;

$R^2$ is hydrogen, alkyl of 1 to 10 carbons, cycloalkyl of 5 to 10 carbons or aralkyl of 7 to 12 carbons;

$R^4$ is hydrogen, primary or secondary alkyl of 1 to 8 carbons, cycloalkyl of 5 to 12 carbons or aralkyl of 7 to 12 carbons.

3. The compound of claim 2 where R is hydrogen, alkyl of 1 to 4 carbons, alkenyl of 3 to 5 carbons, benzyl, 2-cyanoethyl, acetyl, or benzoyl, $R^1$ is hydrogen or methyl, $R^2$ is hydrogen, alkyl of 1 to 4 carbons, or 2,2,6,6-tetramethyl-4-piperidinyl, $R^3$ is a direct bond, an alkylene diradical of 1 to 8 carbons, or an o-, m- or p-phenylene diradical, and $R^4$ is hydrogen.

4. The compound of claim 3 where R is hydrogen, methyl, or acetyl, $R^1$ is hydrogen, $R^2$ is hydrogen or 2,2,6,6-tetramethyl-4-piperidinyl and $R^3$ is a direct bond, an alkylene diradical of 1 to 7 carbons, or a 1,2-ethylene diradical.

5. The compound of claim 4 where R, $R^1$ and $R^2$ are hydrogen and $R^3$ is a direct bond.

6. The compound of claim 4 where R, $R^1$ and $R^2$ are hydrogen and $R^3$ is a 1,2-ethylene diradical.

7. The compound of claim 4 where R is methyl or acetyl, $R^1$ and $R^2$ are hydrogen and $R^3$ is a direct bond.

8. The compound of claim 3 where R, $R^1$ and $R^2$ are hydrogen and $R^3$ is an aklylene diradical of 1–8 carbons.

9. The compound of claim 1 where R, $R^1$ and $R^4$ are hydrogen, $R^3$ is a 1,2-ethylene diradical and $R^2$ is a methylene group linked to $R^3$ to form a 5-membered lactam ring.

* * * * *